United States Patent [19]

Cortes

[11] Patent Number: 5,281,726

[45] Date of Patent: Jan. 25, 1994

[54] 4-HYDROXY-2'-NITROBUTYROPHENONE AND TETRAHYDRO-2-(O-NITROPHENYL)-2-FURANOL USEFUL AS INTERMEDIATES IN THE PREPARATION OF A CROP-SELECTIVE HERBICIDE

[75] Inventor: David A. Cortes, Fairless Hills, Pa.

[73] Assignee: American Cyanamid Company, Wayne, N.J.

[21] Appl. No.: 997,844

[22] Filed: Dec. 29, 1992

[51] Int. Cl.$^5$ .................... C07D 307/20; C07C 49/80; C07C 49/82
[52] U.S. Cl. .................. 549/475; 568/335; 568/336
[58] Field of Search ................ 568/335, 336; 549/475

[56] References Cited

U.S. PATENT DOCUMENTS 4,075,346  2/1978  Sasajima et al. .................... 514/327
5,009,699  4/1991  Brady et al. ........................ 504/214

Primary Examiner—C. Warren Ivy
Assistant Examiner—A. Owens
Attorney, Agent, or Firm—Peggy A. Climenson

[57] ABSTRACT

There are provided 4-Hydroxy-2'-nitrobutyrophenone and tetrahydro-2-(o-nitrophenyl)-2-furanol and mixtures thereof, important intermediates in the preparation of the crop-selective herbicidal agent 1-{[o-(cyclopropylcarbonyl)phenyl]sulfamoyl}-3-(4,6-dimethoxy-2-pyrimidinyl)urea. Also provided is a method for the preparation of 4-halo-2'-nitrobutyrophenone, useful as an intermediate in the preparation of 1-{[o-(cyclopropylcarbonyl)phenyl]sulfamoyl}-3-(4,6-dimethoxy-2-pyrimidinyl)urea.

17 Claims, No Drawings

4-HYDROXY-2'-NITROBUTYROPHENONE AND TETRAHYDRO-2-(O-NITROPHENYL)-2-FURANOL USEFUL AS INTERMEDIATES IN THE PREPARATION OF A CROP-SELECTIVE HERBICIDE

BACKGROUND OF THE INVENTION

The crop-selective herbicidal agent 1-{[o-(cyclopropylcarbonyl)phenyl]sulfamoyl}-3-(4,6-dimethoxy-2-pyrimidinyl)urea is described in U.S. Pat. No. 5,009,699. This sulfamoyl urea compound demonstrates a superior margin of safety toward crop plants, especially rice plants, while concomitantly controlling broadleaf weeds and sedges.

4-Halo-2'-nitrobutyrophenone compounds and their preparation via the reaction of dihydro-3-(o-nitrobenzoyl)-2(3H)-furanone and a hydrogen halide is described in U.S. Pat. No. 4,075,346. However, this patent does not describe 4-hydroxy-2'-nitrobutyrophenone or tetrahydro-2-(o-nitrophenyl)-2-furanol or mixtures thereof. It has now been found that 4-hydroxy-2'-nitrobutyrophenone or tetrahydro-2-(o-nitrophenyl)-2-furanol or mixtures thereof are useful in the preparation of 4-halo-2-nitrobutyrophenone compounds, important intermediates in the preparation of the crop-selective herbicidal agent 1-{[o-(cyclopropylcarbonyl)phenyl]sulfamoyl}-3-(4,6-dimethoxy-2-pyrimidinyl)urea.

It is been an object of the present invention to provide 4-hydroxy-2'-nitrobutyrophenone and tetrahydro-2-(o-nitrophenyl)-2-furanol and mixtures thereof.

It is also an object of the present invention to provide a method for the preparation of 4-halo-2'-nitrobutyrophenone compounds, useful intermediates in the preparation of the sulfamoyl urea crop-selective herbicidal agent.

These and other objects of the invention will become more apparent from the detailed description set forth below.

SUMMARY OF THE INVENTION

The present invention relates to 4-hydroxy-2'-nitrobutyrophenone and tetrahydro-2-(o-nitrophenyl)-2-furanol and mixtures thereof useful as intermediates in the preparation of the crop-selective herbicidal agent 1-{[o-(cyclopropylcarbonyl)phenyl]sulfamoyl}-3-(4,6-dimethoxy-2-pyrimidinyl)urea. The present invention also relates to a method for the preparation of 4-halo-2'-nitrobutyrophenone compounds. The 4-halo-2'-nitrobutyrophenone compounds are also important intermediates in the preparation of said crop-selective herbicidal agent.

DETAILED DESCRIPTION OF THE INVENTION

The present invention describes 4-hydroxy-2'-nitrobutyrophenone and tetrahydro-2-(o-nitrophenyl)-2-furanol and mixtures thereof and their use in a method for the preparation of 4-halo-2'-nitrobutyrophenone compounds. 4-Halo-2'-nitrobutyrophenone compounds and their use in the manufacture of the crop-selective herbicidal agent 1-{[o-(cyclopropylcarbonyl)phenyl]sulfamoyl}-3-(4,6-dimethoxy-2-pyrimidinyl)urea are described in co-pending U.S. patent application Ser. No. 07/909,258 filed Jul. 6, 1992.

4-Hydroxy-2'-nitrobutyrophenone or tetrahydro-2-(o-nitrophenyl)-2-furanol or mixtures thereof may be prepared by reacting dihydro-3-(o-nitrobenzoyl)-2(3H)-furanone with an acid such as sulfuric acid, phosphoric acid or acetic acid, in the presence of a solvent such as water or mixtures of water and an organic solvent. The reaction is carried out preferably from about 40° C. to about 130° C., more preferably from about 50° C. to 90° C. The reaction is shown in Flow Diagram I.

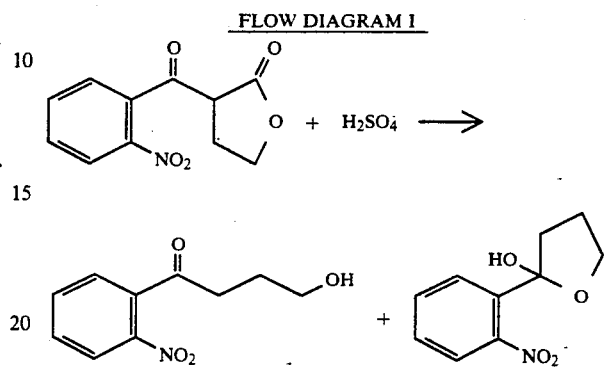

A mixture of 4-hydroxy-2'-nitrobutyrophenone and tetrahydro-2-(o-nitrophenyl)-2-furanol may also be prepared by reacting a $C_1$-$C_4$ alkyl 2-(o-nitrobenzoyl)acetate compound with at least one molar equivalent of a 2-haloethanol, preferably 2-chloroethanol or 2-bromoethanol, in the presence of an aqueous base such as aqueous sodium hydroxide or sodium carbonate, and a phase transfer catalyst, and in the presence of a solvent such as water or a mixture of water and an organic solvent. Typical phase transfer catalysts include benzyltrimethylammonium hydroxide, tetraethylammonium hydroxide and tetrabutylammonium hydroxide. The reaction is carried out preferably from about 25° C. to 130° C., more preferably from about 50° C. to 90° C. The reaction is illustrated in Flow Diagram II.

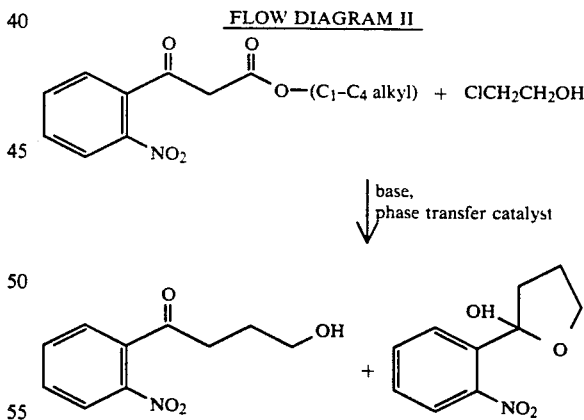

Alternatively, a tautomeric mixture of 4-hydroxy-2'-nitrobutyrophenone and tetrahydro-2-(o-nitrophenyl)-2-furanol may be prepared by reacting a $C_1$-$C_4$ alkyl 2-(o-nitrobenzoyl)acetate compound with at least about one molar equivalent of a 1,2-dihaloethane compound in the presence of a base such as sodium hydroxide and a phase transfer catalyst such as benzyltrimethylammonium hydroxide to form 1-(o-nitrobenzoyl)cyclopropanecarboxylic acid which is reacted with sulfuric acid to form the desired butyrophenone/furanol mixture. The reaction scheme is shown in Flow Diagram III wherein X is Cl, Br or I.

FLOW DIAGRAM III

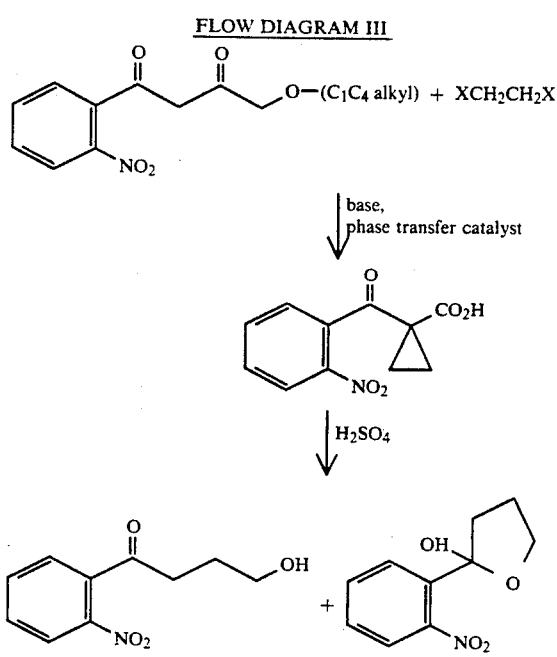

As illustrated in Flow Diagrams I, II and III, the reaction product obtained is a tautomeric mixture of 4-hydroxy-2'-nitrobutyrophenone and tetrahydro-2-(o-nitrophenyl)-2-furanol. The tautomeric ratio formed is dependent upon the solvent system used. For example, in the absence of a solvent or in the presence of an non-aqueous, organic solvent system such as chloroform, methylenechloride, methanol, ethanol, tetrahydrofuran or toluene, the ring-closed furanol tautomer is predominant. However, in the presence of an aqueous solvent system, i.e. water or mixtures of water and a water miscible organic solvent such as methanol, ethanol, acetone, acetonitrile or tetrahydrofuran, the formation of the open-chain hydroxybutyrophenone tautomer is favored. In solvent mixtures of water and non-miscible organic solvents such as toluene, chloroform or methylene chloride where the partition coefficient favors the organic phase, the ring-closed furanol tautomer is favored, while the amount which remains in the aqueous phase will be in the open-chain tautomeric form.

Advantageously, the tautomeric mixtures of 4-hydroxy-2'-nitrobutyrophenone and tetrahydro-2-(o-nitrophenyl)-2-furanol may be used to prepare 4-halo-2'-nitrobutyrophenone compounds, useful as crop-selective, herbicide intermediates. The compounds, 4-hydroxy-2'-nitrobutyrophenone or tetrahydro-2-(o-nitrophenyl)-2-furanol or mixtures thereof may be treated with a hydrogen halide such as hydrogen chloride, hydrogen bromide or more preferably concentrated hydrochloric acid, optionally in the presence of a solvent or mixture of solvents such as water and/or an organic solvent such as aromatic hydrocarbons, chlorinated hydrocarbons or ethers preferably at a temperature of from about 40° C. to about 130° C., to give the desired 4-halo product as shown in Flow Diagram IV wherein X is halogen. The preferred solvent systems are water, toluene and mixtures of water and toluene. In a preferred embodiment, an excess of the hydrogen halide is employed, in other words, the molar ratio of the hydrogen halide to the 4-hydroxy-2'-nitrobutyrophenone, tetrahydro-2-(o-nitrophenyl)-2-furanol or mixtures thereof is greater than one.

FLOW DIAGRAM IV

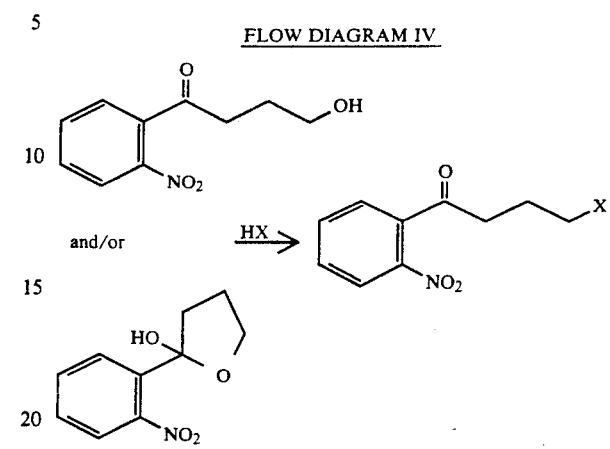

The compounds of the invention or mixtures thereof may also be used to prepare o-aminophenyl cyclopropyl ketone, a key intermediate in the manufacture of the crop-selective herbicide 1-{[o-(cyclopropylcarbonyl)-phenyl]sulfamoyl}-3-(4,6-dimethoxy-2-pyrimidinyl-)urea, as shown in Flow Diagram V wherein X is halogen.

FLOW DIAGRAM V

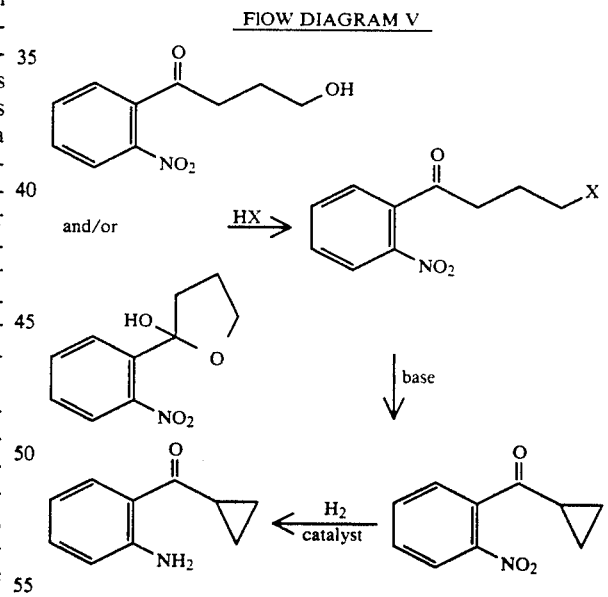

In order to facilitate a further understanding of the invention, the following examples are presented primarily for the purpose of illustrating more specific details thereof. The invention should not be deemed limited thereby except as defined in the claims. The term HPLC designates high performance liquid chromatography. The terms $^1$HNMR and $^{13}$CNMR designate proton and carbon-13 nuclear magnetic resonance, respectively. Unless otherwise noted, all parts are by weight.

EXAMPLE 1

Preparation of 4-Hydroxy-2'-nitrobutyrophenone and tetrahydro-2-(o-nitrophenyl)-2-furanol

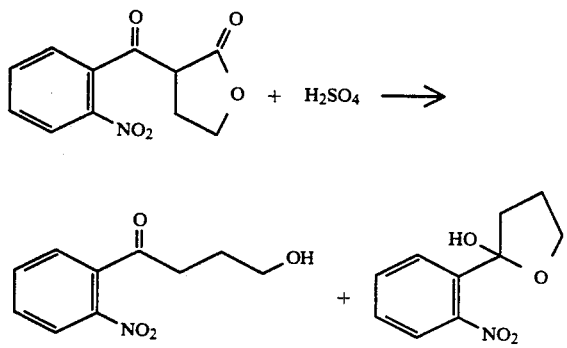

A mixture of dihydro-3-(o-nitrobenzoyl)-2(3H)-furanone (5.6 g, 24 mmol) and sulfuric acid (7.3 g, 96% real, 70 mmol) in water (20 mL) is stirred at 55°-91° C. for 2-3 hours, cooled and extracted with methylene chloride. The combined organic extracts are concentrated in vacuo to give a mixture of the title products (6.1 g) which is identified by $^1$H and $^{13}$CNMR analyses.

EXAMPLE 2

Preparation of 4-Chloro-2'-nitrobutyrophenone

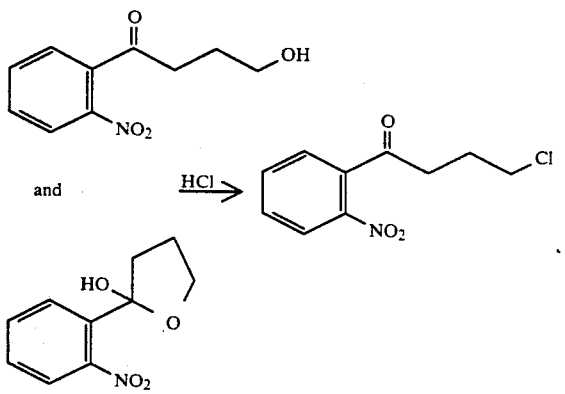

A solution of the mixture obtained in Example 1 (0.5 g) in toluene (2 mL) and 5 mL of 37% HCl is heated at reflux temperature for 1-2 hours and cooled to give the title product, 90% pure by HPLC analysis.

EXAMPLE 3

Preparation of 4-Hydroxy-2'-nitrobutyrophenone

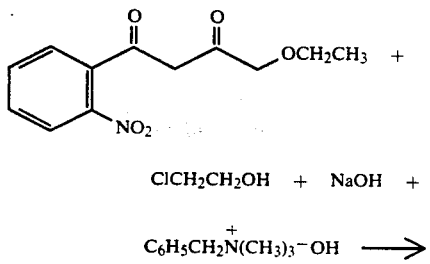

ClCH$_2$CH$_2$OH + NaOH +

C$_6$H$_5$CH$_2$N(CH$_3$)$_3{}^+$OH$^-$ ⟶

-continued

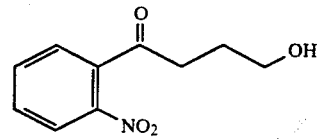

A mixture of ethyl 2-(o-nitrobenzoyl)acetate (11.9 g, 0.05 mol), 2-chloroethanol (8 g, 0.1 mol), 50% sodium hydroxide solution (8.8 g, 4.4 g real, 0.11 mol) and 40% benzyltrimethylammonium hydroxide solution (4.2 g, 1.7 g, real, 0.01 mol) in water (50 mL) is heated at 50°-65° C. for 4-8 hours, cooled and extracted with methylene chloride. The combined organic extracts are concentrated in vacuo to give the title product, identified by $^1$HNMR and $^{13}$CNMR analyses.

I claim:

1. 4-Hydroxy-2'-nitrobutyrophenone.
2. Tetrahydro-2-(o-nitrophenyl)-2-furanol.
3. A method for the preparation of a 4-halo-2'-nitrobutyrophenone compound having the structural formula

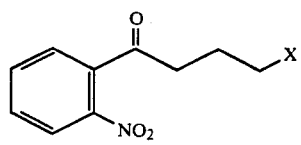

wherein X is halogen; which comprises reacting 4-hydroxy-2'-nitrobutyrophenone or tetrahydro-2-(o-nitrophenyl)-2-furanol or a mixture thereof with a hydrogen halide optionally in the presence of a solvent or solvent mixture to form the 4-halo-2'-nitrobutyrophenone compound.

4. The method according to claim 3 wherein the hydrogen halide is hydrogen chloride.
5. The method according to claim 3 wherein the hydrogen halide is hydrogen bromide.
6. The method according to claim 3 wherein an excess of the hydrogen halide is employed.
7. The method according to claim 3 wherein the solvent is water.
8. The method according to claim 3 wherein the solvent is an aromatic hydrocarbon.
9. The method according to claim 8 wherein the aromatic hydrocarbon solvent is toluene.
10. The method according to claim 3 wherein the solvent mixture is comprised of water and an aromatic hydrocarbon.
11. The method according to claim 10 wherein the aromatic hydrocarbon is toluene.
12. The method according to claim 3 wherein the temperature of the reaction mixture is about 40° C.-130° C.
13. A method for the preparation of a 4-halo-2'-nitrobutyrophenone compound having the structural formula

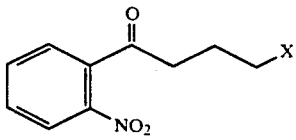

wherein X is halogen; which comprises reacting a compound of the formula

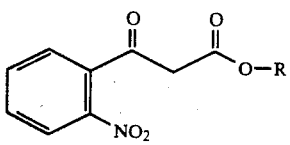

wherein R is $C_1$–$C_4$ alkyl, with a 2-haloethanol compound of the formula

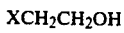

XCH$_2$CH$_2$OH wherein X is chlorine or bromine, in the presence of an aqueous base and a phase transfer catalyst, optionally in the presence of an organic solvent to form 4-hydroxy-2'-nitrobutyrophenone or tetrahydro-2-(o-nitrophenyl)-2-furanol or mixtures thereof and further reacting the 4-hydroxy-2'-nitrobutyrophenone or the tetrahydro-2-(o-nitrophenyl)-2-furanol or the mixture thereof with a hydrogen halide to form the 4-halo-2'-nitrobutyrophenone compound.

14. The method according to claim 13 wherein at least one molar equivalent of the 2-haloethanol compound is employed.

15. The method according to claim 13 wherein the phase transfer catalyst is benzyltrimethylammonium hydroxide and the aqueous base is sodium hydroxide.

16. A method for the preparation of a 4-hydroxy-2'-nitrobutyrophenone or tetrahydro-2-(o-nitrophenyl)-2-furanol or mixtures thereof which comprises reacting dihydro-3-(o-nitrobenzoyl)-2(3H)-furanone with an aqueous acid selected from the group consisting of sulfuric acid, phosphoric acid and acetic acid, optionally in the presence of an organic solvent.

17. A method for the preparation of 4-hydroxy-2'-nitrobutyrophenone or tetrahydro-2-(o-nitrophenyl)-2-furanol or mixtures thereof which comprises reacting a compound of the formula

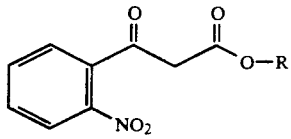

wherein R is $C_1$–$C_4$ alkyl, with a 2-haloethanol compound of the formula

XCH$_2$CH$_2$OH wherein X is chlorine or bromine, in the presence of an aqueous base and a phase transfer catalyst, optionally in the presence of an organic solvent to form 4-hydroxy-2'-nitrobutyrophenone or tetrahydro-2-(o-nitrophenyl)-2-furanol or mixtures thereof.

* * * * *